United States Patent [19]

Hansen

[11] 4,424,715

[45] Jan. 10, 1984

[54] ULTRASONIC MEASURING DEVICE

[75] Inventor: Henning M. Hansen, Nordborg, Denmark

[73] Assignee: Danfoss A/S, Nordborg, Denmark

[21] Appl. No.: 275,809

[22] Filed: Jun. 22, 1981

[30] Foreign Application Priority Data

Jul. 8, 1980 [DE] Fed. Rep. of Germany ....... 3025788

[51] Int. Cl.$^3$ .............................................. G01F 1/66
[52] U.S. Cl. .................................................. 73/861.28
[58] Field of Search ......................... 73/861.18, 861.28

[56] References Cited

U.S. PATENT DOCUMENTS

| | | | |
|---|---|---|---|
| 2,724,269 | 11/1955 | Kalmus ............................ | 73/861.28 |
| 3,835,704 | 9/1974 | Elazar et al. ...................... | 73/861.28 |
| 4,164,865 | 8/1979 | Hall et al. ......................... | 73/861.28 |
| 4,202,210 | 5/1980 | Multon et al. ................... | 73/861.28 |
| 4,312,238 | 1/1982 | Rey ................................... | 73/861.28 |

Primary Examiner—Charles A. Ruehl

Attorney, Agent, or Firm—Wayne B. Easton

[57] ABSTRACT

The apparatus herein relates to an ultrasonic measuring device having a quadrupole circuit unit. Two ultrasonic converter circuits are alternately and complementary operable as transmitter and receiver circuits and have terminals on opposite sides of the quadrupole circuit unit. The quadrupole circuit unit has a transmission signal generator on the input side thereof and a receiver amplifier on the output side thereof. This kind have a zero point displacement which becomes noticeable by the fact that during a measurement in static liquid the measured signal has different values depending on the direction. As only one transmission signal generator and only one receiver amplifier are used, these values cannot be eliminated as is possible in the case of known constructions with two transmitters. This problem is dealt with by forming substantially equal terminating impedances of the quadrupole formed by both ultrasonic conveyor circuits and by providing the transmission signal generator in the form of a current generator.

8 Claims, 4 Drawing Figures

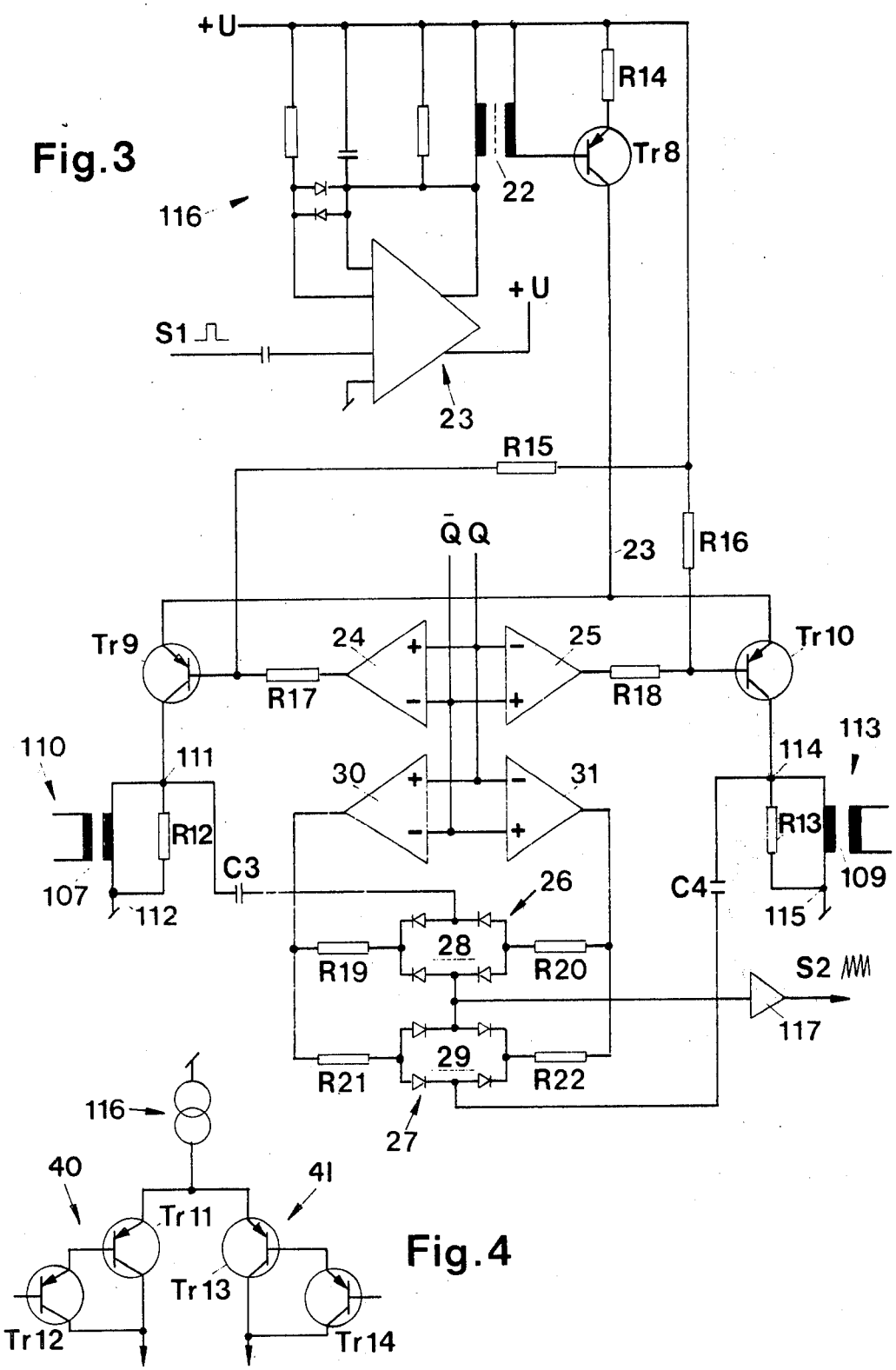

ULTRASONIC MEASURING DEVICE

The invention relates to an ultrasonic measuring device comprising two ultrasonic converter circuits which are selectively operative as transmitter and receiver and the terminals of which are selectively operatively connectable by a switch-over device to a transmission signal generator or a receiver amplifier.

In a known measuring device of this kind (U.S. Pat. No. 3,818,757), the transmission signal generator is connected by a respective first switch and the receiver amplifier by way of a respective second switch to the one terminal of each ultrasonic converter circuit. By alternately switching these switches on and off in pairs, the measuring path is traversed by the ultrasonic signal in the one or other direction.

Such devices have many uses. For example, they are used for the ultrasonic measurement of the speed of flowing media. In this case, the measuring path is so designed that at least one component of the flow velocity extends in the direction of the ultrasonic signal during the one measurement and in the opposite direction during the other measurement. In operation, it has been found that in a measuring device of the aforementioned kind there is often a zero point displacement which becomes noticeable by the fact that during a measurement in static liquid the measured signal has different values depending on the direction. Since only one transmission signal generator and one receiver amplifier are used, these values cannot be eliminated as is possible in the case of known constructions with two transmitters.

The invention is based on the object of providing an ultrasonic measuring device of the aforementioned kind in which the undesired zero point displacement is considerably reduced and, in the most favourable case, practically completely eliminated.

This problem is solved according to the invention in that, for forming practically equal terminating impedances of the quadrupole formed by both ultrasonic converter circuits, the transmission signal generator is in the form of a current generator.

In this solution, the two ultrasonic convertor circuits including the transmission transformers, the connecting cable and the measuring path therebetween are regarded as a quadrupole consisting of elements having an impedance independent of the amplitude and direction of the signal. For such a quadrupole, its transmission function is independent of whether the quadrupole is reversed, provided that the terminating impedances are equal. This reversal of the quadrupole corresponds exactly to that which happens when the ultrasonic converter circuits are alternately used on the transmission side and on the receiver side. By reason of the fact that a current generator is used as the transmission signal generator, it is possible to give the transmission signal generator and the receiver amplifier an impedance of the same order and in this way produce practically equal terminating impedances. In this way it is possible, solely with the internal impedances of the transmission signal generator and receiver amplifier or in conjunction with further impedances, to keep the terminating resistances on both sides of the quadrupole practically equal and thereby to reduce or even completely eliminate the disruptive zero point displacement. In this construction one obtains equal transmission conditions in both directions even if, for example, the impedances of the ultrasonic converter circuits are not strictly equal for manufacturing reasons or if these circuits age differently in the course of time, for example through soiling of the measuring path. Reflections are likewise transmitted independently of direction. Further, the switching means can be so designed that they have practically no influence on a zero point displacement.

It is also favourable if the terminals of both ultrasonic converter circuits are provided in both switching positions with at least one load impedance which are small compared with the impedance of the current generator and of the receiver amplifier. These impedances can contribute to obtaining equal terminating resistances, serve for adaptation purposes or facilitate inclusion of the switching means.

In the simplest case, the load impedances are ohmic resistors which can be made cheaply and imployed with accurate values. However, one can also consider load impedances in the form of coils, condensers and the like if they are linear and independent of amplitude, or combinations of different impedances.

Above all, the load impedances can be so dimensioned that they damp the inherent resonance of the ultrasonic converter circuits.

A preferred embodiment is characterized in that the current generator is connected to the one terminal of the two ultrasonic converter circuits by way of a respective load impedance, the receiver amplifier is connected to the other terminal of the two ultrasonic converter circuits by way of a respective load impedance, and all terminals are earthed by way of a respective switch, all the load impedances being equal. By switching the diagonally disposed switches on and off in pairs, the switches preferably being transistor switches, the ultrasonic converter circuits and the associated load resistors are made effective respectively in the transmission side or receiver side sense. This results in a simple circuit in which all the switches are earthed at one side. The load impedances form the equal terminating resistances in respective pairs. The high ohmic internal resistances of the current generator and of the receiver amplifier can be neglected in relation to these terminating resistances.

In another preferred circuit, each of two at least approximately equal load impedances is in parallel with the terminals of the ultrasonic converter circuits. In this case the load impedances are fixed to the terminals of a respective one ultrasonic converter circuit and can therefore be regarded as part of the quadrupole of which the terminating resistances are then formed by the very high internal impedances of the current generator and receiver amplifier. Since the load resistances need in this case not be precisely equal, they can be very accurately adapted to the damping of the resonance frequency of each ultrasonic converter circuit.

The first switches may be transistor switches. It is particularly advisable for them to be formed by a respective Darlington transistor circuit. In such a circuit it is ensured that practically the entire current flows through the collector-emitter path and there is therefore good insulation with respect to the base.

The second switches are preferably formed by a current-controlled diode bridge. This likewise has a very low resistance, particularly in comparison with the high ohmic receiver amplifier.

In some cases it is desirable for the current generator to comprise a keyed oscillator. When this oscillates, one can achieve stronger excitation.

The invention will now be described in more detail with reference to preferred examples illustrated in the drawing, wherein:

FIG. 3 is the circuit diagram of a second embodiment of an ultrasonic measuring device according to the invention, and FIG. 4 is a modification of part of this circuit.

Figures 1, 2:
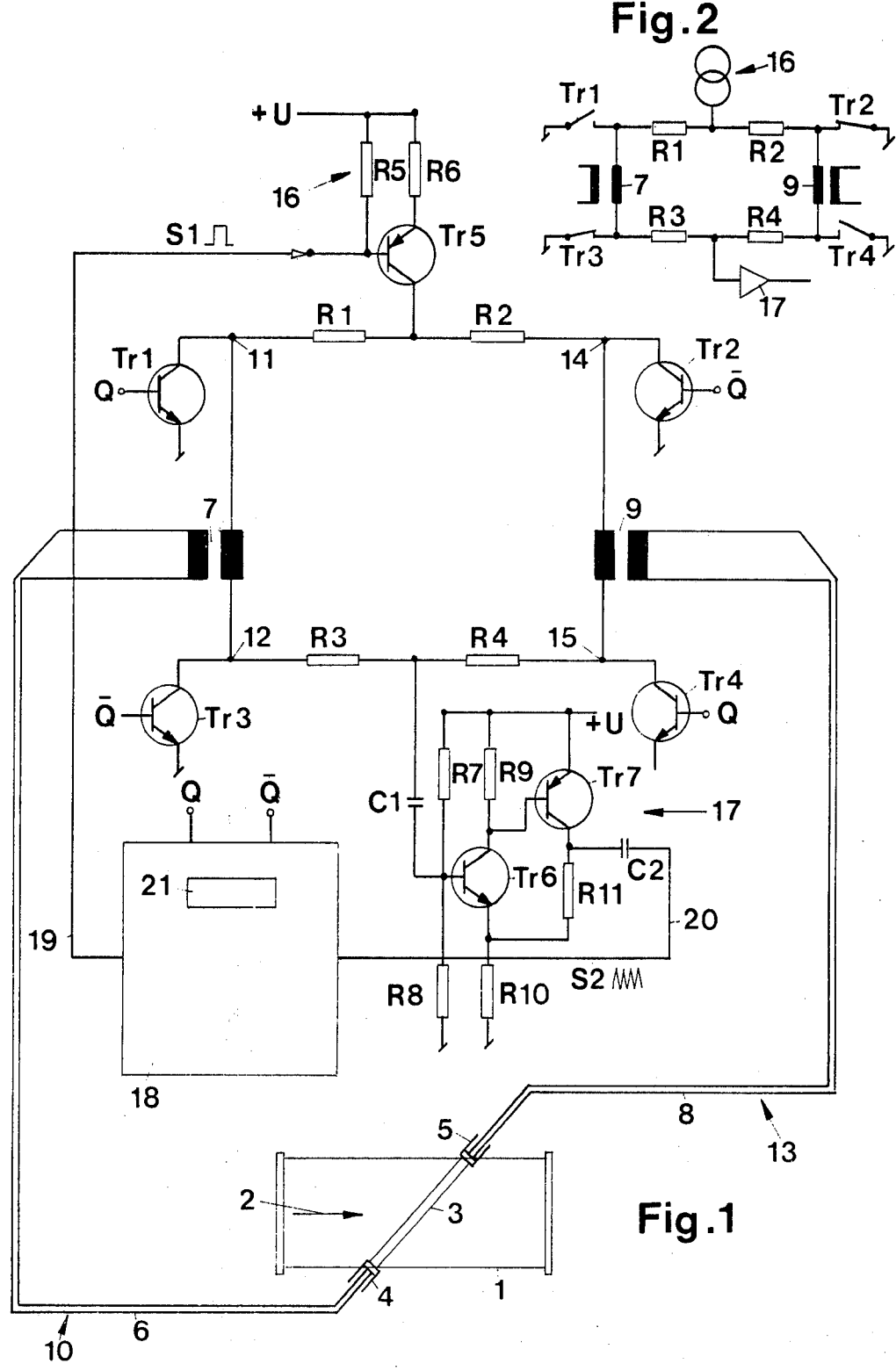
FIG. 1 is a circuit diagram of a first embodiment of an ultrasonic measuring device according to the invention.
FIG. 2 is a simplified representation of the same circuit.

In the embodiment of FIG. 1, a measuring path 3 closed at both ends by an ultrasonic converter 4 or 5 of conventional construction is provided in a tube 1 in which liquid flows in the direction of the arrow 2. The ultrasonic converter 4 is connected by way of a coaxial conduit 6 to a transformer 7 and the converter 5 is connected by way of a coaxial conduit 8 to a transformer 9. The components 4, 6 and 7 form a first ultrasonic converter circuit 10 with two terminals 11 and 12. The components 5, 8 and 9 form a second ultrasonic converter circuit 13 with the terminals 14 and 15.

The terminals 11 and 14 are interconnected by way of two ohmic load resistors R1 and R2 and the terminals 12 and 15 by way of two ohmic load resistors R3 and R4. Each terminal is earthed by way of a transistor switch Tr1, Tr2, Tr3 or Tr4.

Between the resistors R1 and R2 there is a transmission signal generator 16 in the form of a current generator with a switching transistor Tr5, a base resistor R5 and an emitter resistor R6. Between the resistors R3 and R4 there is connected by way of a condenser C1 a receiver amplifier 17 comprising two transistors Tr6 and Tr7, the resistors R7, R8, R9, R10 and R11 as well as the output condenser C2. A control and evaluating device 18 transmits to the switching transistor Tr5 of the current generator 16 an operating pulse s1 by way of a conduit 19 and receives by way of the conduit 20 the high frequency receiver signal S2 from the receiver amplifier 17. In addition, the device 18 delivers control pulses Q and $\overline{Q}$ to the transistor switches Tr1 to Tr4 to bring these into the conductive state alternately in pairs. The measuring result can for example be displayed in the area 21.

The ohmic load resistors R1 and R2 are equal but small in relation to the impedance of the current generator 16 which is primarily determined by the resistor R6. The ohmic load resistors R3 and R4 are equal but small in relation to the impedance of the receiver amplifier 17 which is primarily determined by the resistor R8.

The operation is as follows: When the control signal $\overline{Q}$ is transmitted, one obtains the operating condition of FIG. 2. The current delivered by the current generator 16 is divided into two parts, of which one flows through the series circuit of the load resistor R1 and transformer 7 and the other through the load resistor R2. The signal on the receiver side delivered through the transformer 9 flows through the series circuit of the load resistors R4 and R3, which serve as a voltage divider, so that the receiver amplifier 17 is controlled by the voltage drop at the load resistor R3. In this circuit, the two ultrasonic converter circuits 10 and 13 form a quadrupole between their terminals 11, 12 and 14, 15, variations in the impedance within the quadrupole having practically no effect on the power output of the current generator. This is because its current is practically exclusively determined by the resistor R6. The terminating impedance of the quadrupole on the input side is small, being given by the parallel circuit of the load resistor R2 and R1 at the input of the quadrupole. The terminating impedance on the output side is of the same value and given by the resistors R3 and R4. Upon switching the control signal Q over and renewed delivery of the operating pulse s1, the transmission pulse is delivered through the transformer 9 and the receiving signal through the transformer 7. This results in the same conditions. In this way, a disruptive zero point displacement is practically entirely suppressed.

In the FIG. 3 embodiment, of the ultrasonic converter circuits 110 and 113, only the transformers 107 and 109 are illustrated with the associated terminals 111 and 112 or 114 and 115. The transmission signal generator 116 has a construction differing from that in FIG. 1 but the receiveramplifier 117 can have the same construction.

In this construction, an ohmic load resistor R12 is connected between the terminals 111 and 112 and an ohmic load resistor 113 between the terminals 114 and 115. Both resistors are preferably of equal size but small in relation to the impedances of the transmission signal generator 116, which is again a current generator, and of the receiver amplifier 117. The load resistors at the same time serve to damp the resonances of the ultrasonic converter circuit, which could result in overcontrol and non-linearity in the switching means.

The current generator 116 comprises a transistor Tr8 with an emitter resistor R14. Its base is influenced by way of a transformer 22 by an oscillator circuit 23 of conventional construction which is controlled by the operating pulse s1, so that the current generator delivers a current oscillation as a transmission signal.

The output conduit 23 of the current generator 116 is connected to the terminal 111 by way of a transistor switch Tr9 and to the terminal 114 by way of a transistor switch Tr10. The base of these first switches is normally applied to the positive feed voltage by way of the resistors R15 or R16, so that these switches are blocked. They can be applied to the negative potential to become conductive by means of the signals Q or $\overline{Q}$ by way of amplifiers 24 or 25 and associated resistors R17 or R18.

The terminal 111 is connected by way of a condenser C3 to a switch 26 and the terminal 114 by way of a condensor C4 to a switch 27. The switch outputs lead to the receiver amplifier 117. These two second switches are each formed by a diode bridge 28 or 29 preceded and followed by resistors R19, R20 or R21, R22. These switches are operated by amplifiers 30 or 31 with the aid of the signals Q or $\overline{Q}$. If, for example, the amplifier 30 exhibits a positive output and the amplifier 31 a negative output, current flows through the switch 27 with the result that an output signal can be transmitted from the terminal 114 to the receiver amplifier 117. The circuit is so selected that the transistor switch Tr9 is at the same time conductive. Upon reversal of the signal, the transistor switch Tr10 becomes conductive and the switch 28 ensures transmission of the receiver signal.

In this circuit, the load resistors R12 and R13 can be regarded as part of the quadrupole so that the equal terminating impedances are formed by the very high internal resistances of the current generator 116 and receiver amplifier 117. The current generator 116 which has a high resistance because of its resistor R14 is loaded by a very low impedance because a low load resistance is connected in parallel to the input side of the quadrupole formed between the terminals 111, 112 and 114, 115 whereas the quadrupole is terminated on the output side by a low resistance.

In the FIG. 4 embodiment, the two transistor switches Tr9 and Tr10 are replaced by a Darlington Circuit 40 or 41 each consisting of two transistors Tr11 and Tr12 or Tr13 and Tr14. This circuit has the advantage that only a small part of the switching current flows through the base so that non-linearities of these switches likewise have no influence on the measuring result.

Many departures are possible from the illustrated examples. For example, the second switches 26 and 27 can likewise be replaced by simple transistor switches.

In one practical embodiment of the FIG. 1 circuit, the load resistors R1 to R4 each had a value of 100 ohms. The impedance of the current generator 16 was about 50k ohms. For the receiver amplifier, the resistor R7 had a value of 200k ohms and the resistor R8 a value of 33k ohms.

What is claimed is:

1. An ultrasonic measuring unit, comprising, quadrupole circuit means, two ultrasonic converter circuits which are alternately and complementary operable as transmitter and receiver circuits, said two converter circuits each having terminals on opposite sides of said quadrupole circuit means, said quadrupole circuit means having terminating load impedances for said ultrasonic converter circuits, said quadrupole circuit means having a transmission signal generator in the form of a current generator on the input side thereof and a receiver amplifier on the output side thereof, switching means for said quadrupole circuit means for alternating the operation of said converter circuits, said load impedances being small compared with the impedances of said current generator and of said receiver amplifier for respectively forming substantially equal terminating impedances for said two converter circuits.

2. An ultrasonic measuring unit according to claim 1, characterized in that said load impedances are ohmic resistors.

3. An ultrasonic measuring unit according to claim 1, characterized in that said load impedances dampen the inherent resonance of said ultrasonic converter circuits.

4. An ultrasonic measuring unit according to claim 1, characterized in that said current generator is connected to said converter circuit terminals on the input side of said quadrupole circuit means by way of a first pair of parallel arranged load impedances and said receiver amplifier is connected to said converter circuit terminals on the output side of said quadrupole circuit means by way of a second pair of parallel arranged load impedances, said impedances of said first and second pairs of impedances forming a part of said terminating load impedances, said switching means operating to selectively ground opposite sides of each of said converter circuit terminals.

5. An ultrasonic measuring unit according to claim 1 in which said transmission signal generator is connected to said converter circuit terminals on the input side of said quadrupole circuit means by way of first pair of switch means and said receiver amplifier is connected to said converter circuit terminals on the output side of said quadrupole circuit means by way of a second pair of switch means, said first and second pairs of switch means forming a part of said switching means, and said load impedances including at least two approximately equal load impedances in parallel respectively with said terminals of said two converter circuits.

6. An ultrasonic measuring unit according to claim 5, characterized in that said first switch means are formed by a Darlington transistor circuit.

7. An ultrasonic measuring unit according to claim 6, characterized in that said second switch means are formed by current-controlled diode bridges.

8. An ultrasonic measuring unit according to claim 1, characterized in that said current generator comprises a keyed oscillator.

* * * * *